US008716217B2

(12) United States Patent
Chan et al.

(10) Patent No.: US 8,716,217 B2
(45) Date of Patent: May 6, 2014

(54) POLYGLUTAMIC ACIDS FUNCTIONALIZED BY CATIONIC GROUPS AND HYDROPHOBIC GROUPS AND APPLICATIONS THEREOF, IN PARTICULAR THERAPEUTIC APPLICATIONS THEREOF

(76) Inventors: You-Ping Chan, Ternay (FR); Cecile Bonnet-Gonnet, Lyons (FR); Olivier Breyne, Lyons (FR)

( * ) Notice: Subject to any disclaimer, the term of this patent is extended or adjusted under 35 U.S.C. 154(b) by 503 days.

(21) Appl. No.: 12/149,542

(22) Filed: May 5, 2008

(65) Prior Publication Data
US 2009/0012028 A1 Jan. 8, 2009

Related U.S. Application Data

(60) Provisional application No. 60/924,218, filed on May 3, 2007.

(30) Foreign Application Priority Data

May 3, 2007 (FR) ...................................... 07 03185

(51) Int. Cl.
*A61K 38/00* (2006.01)
*A61K 47/30* (2006.01)
*A61K 48/00* (2006.01)
*C08G 63/00* (2006.01)

(52) U.S. Cl.
USPC ......... 514/1.1; 514/44 R; 514/772.7; 528/184

(58) Field of Classification Search
CPC .................... A61K 2800/57; A61K 47/48315; A61K 8/88; A61Q 19/00; C08G 69/10; C08G 69/48
See application file for complete search history.

(56) References Cited

U.S. PATENT DOCUMENTS

| | | | |
|---|---|---|---|
| 4,351,337 A | 9/1982 | Sidman | |
| 4,652,441 A | 3/1987 | Okada et al. | |
| 4,888,398 A | 12/1989 | Bichon et al. | |
| 5,449,513 A | 9/1995 | Yokoyama et al. | |
| 5,904,936 A | 5/1999 | Huille et al. | |
| 6,153,193 A | 11/2000 | Kabanov et al. | |
| 6,630,171 B1 | 10/2003 | Huille et al. | |
| 6,686,446 B2 * | 2/2004 | Deming et al. | 530/333 |
| 2006/0099264 A1 | 5/2006 | Chan et al. | |
| 2007/0010652 A1 | 1/2007 | Angot et al. | |
| 2007/0128118 A1 * | 6/2007 | Yu et al. | 424/9.322 |
| 2007/0160568 A1 | 7/2007 | Angot et al. | |
| 2007/0178126 A1 | 8/2007 | Angot et al. | |
| 2007/0248686 A1 | 10/2007 | Touraud et al. | |
| 2009/0305948 A1 * | 12/2009 | Soula et al. | 514/8 |
| 2010/0034886 A1 * | 2/2010 | Soula et al. | 424/489 |
| 2010/0048735 A1 * | 2/2010 | Chan et al. | 514/772.1 |

FOREIGN PATENT DOCUMENTS

| | | |
|---|---|---|
| EP | 0 963 758 | 12/1999 |
| EP | 2 206 736 A1 * | 7/2010 |
| FR | 2 801 226 | 5/2001 |
| FR | 2 840 614 | 12/2003 |
| FR | 2 843 117 | 2/2004 |
| JP | 2002/194078 | 7/2002 |
| JP | 2006/077037 | 3/2006 |
| WO | WO 99/61512 | 12/1999 |
| WO | WO 03/104303 | 12/2003 |
| WO | WO 2004/013206 | 2/2004 |
| WO | WO 2004/060968 | 7/2004 |

OTHER PUBLICATIONS

Akiyoshi, K. et al., "Self-Assembled Hydrogel Nanoparticle of Cholesterol-Bearing Pullulan as a Carrier of Protein Drugs: Complexation and Stabilization of Insulin," 1998, *J. Control. Release*, 54(3):313-20.
Yang et al., "Self-Aggregates of Oligoarginine-Conjugated Poly(Amino Acid) Deriatives as a Carrier for Intracellular Drug Delivery," 2005, *Biotechnol. Lett.*, 27(14):977-82.
Shen, W.C., "Acid-Sensitive Dissociation Between Poly(Lysine) and Histamine-Modified Poly(Glutamate) as a Model for Drug-Releasing From Carriers in Endosomes," 1990, *Biochim. Biophys. Acta*, 1034(1):122-24.
Fuller, W. et al., "A Procedure for the Facile Synthesis of Amino-Acid N-Carboxyanhydrides," 1976, *Biopolymers*, 15:1869-71.

* cited by examiner

*Primary Examiner* — Marcela M Cordero Garcia
(74) *Attorney, Agent, or Firm* — Patton Boggs LLP

(57) ABSTRACT

The present invention relates to novel biodegradable materials based on modified polyamino acids that are useful in particular in the vectorization of active principle(s) (APs). The invention is also directed to novel pharmaceutical, cosmetic, health-food or plant-protection compositions based on these polyamino acids.

The aim of the invention is to provide a novel polymeric starting material which can be used for AP vectorization and which satisfy all the requirements: biocompatibility, biodegradability, ability to easily associate with or dissolve numerous active principles and to release these active principles in vivo. This goal is achieved by the present invention, which relates to novel polyglutamates modified by cationic groups, which, if they can be deprotonated, exhibit a pKa equal to or greater than 7, and by hydrophobic groups comprising from 8 to 30 carbon atoms.

These polyglutamates modified by cationic groups are easily and economically converted into particles for the vectorization of active principles, these particles being themselves capable of forming stable aqueous colloidal suspensions. These modified polyglutamates exhibit the advantage of being less viscous than other analogous polymers while retaining an ability to associate proteins, such as insulin. Some are soluble in water at acidic pH and become insoluble at physiological pH (7.4) and should thus, during subcutaneous injection, precipitate on the site of injection.

18 Claims, No Drawings

POLYGLUTAMIC ACIDS FUNCTIONALIZED BY CATIONIC GROUPS AND HYDROPHOBIC GROUPS AND APPLICATIONS THEREOF, IN PARTICULAR THERAPEUTIC APPLICATIONS THEREOF

CROSS-REFERENCE TO RELATED APPLICATIONS

This application claims priority to French Application No. 0703185, filed May 3, 2007, currently pending, and U.S. Provisional Application No. 60/924,218, filed May 3, 2007. The contents of which are incorporated herein in their entirety.

The present invention relates to novel biodegradable materials containing copolyamino acids useful in particular in the vectorization of active principle(s) (APs).

The invention is also directed to novel pharmaceutical, cosmetic, health food or plant-protection compositions containing these modified polyamino acids. These compositions can be of a type that makes possible the vectorization of APs and are preferably provided in the form of emulsions, micelles, nanoparticles, microparticles, gels, implants or films.

Suitable APs are advantageously biologically active compounds which can be administered to an animal or human organism using the oral, parenteral, nasal, vaginal, ocular, subcutaneous, intravenous, intramuscular, intradermal, intraperitoneal, intracerebral or buccal route and the like.

APs to which the invention more particularly but without limitation relates to are proteins, glycoproteins, peptides, polysaccharides, lipopolysaccharides, oligo- or polynucleotides, and organic molecules. However, cosmetic products or plant-protection products, such as herbicides, insecticides, fungicides, and the like, are also envisioned.

In the field of vectorization of active principles, in particular medicinal active principles, there is a need:
  to protect them from decomposition (hydrolysis, enzymatic digestion, and the like),
  and/or to control their rate of release, in order to maintain a therapeutic level over a defined period of time,
  and/or to convey them (while protecting them) to the site of action.

Several types of polymers have been studied for these purposes and some are even commercially available. Examples of such polymers include polylactic, polylactic/glycolic, polyoxyethylene/oxypropylene, polyamino acid or polysaccharide polymers. These polymers are used as starting materials, for example, for the manufacture of bulk implants, microparticles, nanoparticles, vesicles, micelles or gels. Apart from the fact that these polymers have to be suitable for the manufacture of such systems, they also have to be biocompatible, nontoxic, nonimmunogenic and economic, and they have to be able to be easily eliminated from the body and/or to be biodegradable. With regard to the latter aspect, it is moreover essential for the biodegradation in the body to generate nontoxic products.

Various patents, patent applications, and scientific papers are mentioned below by way of illustration of the prior art relating to polymers employed as starting materials for the preparation of AP vectorization systems.

U.S. Pat. No. 4,652,441 describes polylactide microcapsules encapsulating the hormone LH-RH. These microcapsules are produced by preparing a water-in-oil-in-water emulsion comprising an aqueous internal layer comprising the hormone, a substance (gelatin) which fixes the latter, an oily polylactide layer and an aqueous external layer (polyvinyl alcohol). The release of the AP can take place over a period of more than two weeks after subcutaneous injection.

U.S. Pat. No. 6,153,193 describes compositions based on amphiphilic micelles of poly(oxyethylene)-poly(oxypropylene) for the vectorization of anticancer agents, such as doxorubicin.

Akiyoshi et al. (*J. Controlled Release*, 1998, 54, 313-320) describe pullulans which are rendered hydrophobic by grafting cholesterol and which form nanoparticles in water. These nanoparticles, which are capable of reversibly forming a complex with insulin, form stable colloidal suspensions.

U.S. Pat. No. 4,351,337 describes amphiphilic copolyamino acids based on leucine and on glutamate which can be used in the form of implants or of microparticles for the controlled release of active principles. Release of the active principles can take place over a very long period of time depending on the rate of decomposition of the polymer.

U.S. Pat. No. 4,888,398 describes polymers based on polyglutamate or polyaspartate and optionally polyleucine with alkyloxycarbonylmethyl groups placed randomly on the polyamino acid chain. These polyamino acids, grafted with side groups, e.g. methoxycarbonylmethyl groups, can be used in the form of biodegradable implants comprising an AP for sustained release.

U.S. Pat. No. 5,904,936 describes nanoparticles obtained from a polyleucine/polyglutamate block polymer which are able to form stable colloidal suspensions and which are capable of joining together spontaneously with biologically active proteins without denaturing them. The active proteins can subsequently be released in vivo in a controlled manner over a long period.

U.S. Pat. No. 5,449,513 describes amphiphilic block copolymers comprising a polyoxyethylene block and a polyamino acid block, for example poly(β-benzyl-L-aspartate). These polyoxyethylene/polybenzylaspartate polymers form micelles which are capable of encapsulating hydrophobic active molecules, such as doxorubicin or indomethacin.

Patent application WO-A-99/61512 describes polylysines and polyornithines functionalized with a hydrophobic group (palmitic acid connected to the polylysine or -ornithine) and a hydrophilic group (polyoxyethylene). These polymers, for example polylysine grafted with polyoxyethylene and palmitoyl chains, form, in the presence of cholesterol, vesicles capable of encapsulating doxorubicin or DNA. These polymers based on polylysines are cationic in physiological medium.

Patent application EP-A-963 758 describes polyamino acids functionalized by a cationic group. These polymers are capable of forming complexes with a nucleic acid and can be used in gene therapy. The cationic groups are amine derivatives which are not derived from amino acids and the polyamino acids do not comprise hydrophobic groups.

Yang et al. (*Biotechnology Letters*, 2005, 27, 977-982) describe polyaspartates functionalized by linear alkyl groups and oligoarginines. These polymers form nanoparticles from 8 to 40 nm in size in water and are capable of being internalized by cells. It is suggested that these particles can be used for the vectorization of hydrophobic molecules.

In the same field, the present Applicant has described, in several patent applications, polymers based on polyglutamate (anionic polymers) with related concepts.

Application WO-A-03/104303 describes anionic polyamino acids functionalized by α-tocopherol.

Application WO-A-2004/013206 describes anionic polyamino acids comprising hydrophobic groups, wherein these groups are connected to the polymer via a joint comprising two amide functional groups and more specifically via a spacer of lysine or ornithine.

Application WO-A-2004/060968 describes polyamino acids functionalized by at least one oligoamino acid group based on leucine, isoleucine, valine and/or phenylalanine.

The article by W. C. Shen, "Acid-sensitive dissociation between poly(lysine) and histamine-modified poly (glutamate) as a model for drug-releasing from carriers in endosomes", *Biochim. Biophys. Acta,* 1034 (1), 122-124, 1990, describes a polyglutamate functionalized by 40% of histamine. However, this document does not describe any hydrophobized polyglutamate backbone. Furthermore, the polymer described precipitates between pH 4 and 5 and is soluble at physiological pH. The only application that is developed is directed to the formation of complexes with a pH-sensitive polylysine. These complexes are formed through electrostatic interactions. Specifically, at physiological pH, the polyglutamate-histamine/polylysine complex is formed, whereas it decomposes at pH 4-5, which is the pH within in the endosome.

Thus, even if many technical solutions have been developed and described in the prior art for the vectorization of medicinal active principles, the answer to all the requirements is difficult to obtain and remains to be improved. More specifically, the invention relates to biodegradable polyamino acids which can be converted into colloidal nano- or microparticles for vectorization that can reversibly undergo association with active principles.

In this context, one of the essential objectives of the present invention is to provide novel amphiphilic copolyglutamates comprising both positive charges at neutral pH or pH close to neutrality and hydrophobic groups as a pendant (or hanging) chain.

These polymers represent an improvement, with respect to those described in the patents or patent applications mentioned above, in terms of vectorization of an active principle, such as a therapeutic peptide or protein, a DNA, an RNA or a small molecule.

Another objective of the present invention is for these polymers to be useful in the vectorization of active principles (APs) and to optimally satisfy all the specifications of the requirements, namely, in particular:

ability:
to easily and economically form stable aqueous colloidal suspensions,
to easily associate with numerous active principles, and to release these active principles in vivo,
biocompatibility,
biodegradability,
stability to hydrolysis.

This objective, among others, is achieved by the present invention, which relates to polyamino acids, or pharmaceutically acceptable salts thereof, comprising glutamic residues, wherein some of the glutamic residues each carry a pendant cationic group which, if it can be deprotonated, exhibits a pKa equal to or greater than 7, said cationic groups being identical to or different from one another, and wherein other glutamic residues each carry a pendant hydrophobic group (GH), said hydrophobic groups (GH) being identical to or different from one another.

In the description that follows, unless otherwise specified, the term "cationic group" will generally denote cationic groups which cannot be deprotonated and cationic groups which can be deprotonated and which exhibit a pKa equal to or greater than 7.

The term "pharmaceutically acceptable salts" of a polyamino acid according to the invention is understood to encompass all polyamino acids with counterions associated with ionized functions of the polymers.

In the description that follows, the term "small molecule" is understood to mean a molecule with a molecular weight of less than 1 kDa.

Unless otherwise specified, alkyl groups contain 1 to 10 carbon atoms.

Each polyglutamate according to the invention is thus functionalized by a multiplicity of pendant cationic groups that are identical to or different from one another and pendant hydrophobic groups (GH) that are identical to or different from one another.

Within the meaning of the invention, the term "multiplicity" means that the polyglutamate is functionalized by:
at least 1% of cationic groups (molar %, with respect to glutamic acid residues) and up to 99%,
on average, at least two pendant hydrophobic groups (GH) per molecule. It is possible, in accordance with the invention, for a polyglutamic acid to contain, in addition to pendant hydrophobic groups (GH), hydrophobic groups (GH) that are attached to at least one end of the copolymer chains.

Within the meaning of the invention, the expression "to carry" means that the group being carried is pendant, that is to say that said group is a side group with respect to glutamic residues and is a substituent of the functional carbonyl group in the γ position of the glutamic residue which carries it.

Polyglutamates of the invention also carries cationic groups. These groups are preferably attached to the glutamic residues via an amide or ester bond.

According to an alternative embodiment of the invention, other glutamic residues can each carry a pendant nonionizable group, different from the hydrophobic groups (GH), said nonionizable groups being identical to or different from one another. Such a pendant nonionizable group can be, for example, a hydroxyethylamino group.

According to another alternative embodiment of the invention, other glutamic residues can each carry, also in the γ position to the carbonyl, a group which is nonionized at neutral pH, different from the hydrophobic groups (GH), said groups nonionized at neutral pH being identical to or different from one another. For example such a group may have the following formula:

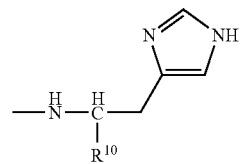

in which —R$^{10}$ is —H, —CO$_2$H, alkyl ester (preferably —COOMe or —COOEt), —CH$_2$OH, —C(=O)—NH$_2$, —C(=O)—NH—CH$_3$ or C(=O)—N(CH$_3$)$_2$.

Polyglutamates simultaneously carrying cationic groups and hydrophobic groups and, optionally, nonionic groups (nonionizable or nonionized at neutral pH), can also comprise negative charges (at neutral pH) resulting from ionization of pendant groups of the polyglutamic acid which have not been functionalized.

The Applicant has developed a novel family of polymers based on polyglutamate carrying cationic groups and functionalized by a multiplicity of hydrophobic groups, which can form stable colloidal systems. The possibility to adjust the loading of the polymer as a function of the degree of functionalization can prove to be very effective in:

lowering the viscosity of the polymer for easier injection or easier use during the formulation stage, providing good association with neutral, anionic or cationic active principles.

Thus, the polymers of the invention can be:

anionic, cationic or neutral and capable of associating with charged or uncharged active principles, cationic at moderately acidic pH (pH=4-5) and neutral or weakly charged at neutral pH. In this case, this dependence on the pH allows them, after association with the active principle in solution at pH=4-5, to form a deposit in a physiological medium.

Furthermore, the polymers of the present invention undergo easy degradation in the presence of enzymes leading to nontoxic catabolites/metabolites (amino acids).

Within the meaning of the invention and throughout the present document, the term "association" or "associate", as used to characterize the relationship between one or more active principles and the modified polyglutamates, means that the active principle or principles is/are bonded or linked to the polyglutamate(s) in particular via a hydrophobic interaction and/or are encapsulated by the polyglutamate(s).

Advantageously, polyamino acids according to the invention are L-glutamate or L-glutamic homopolymers; preferably, within the polyamino acid, these residues are linked by their carboxyl group in alpha position.

The cationic groups which can be used to functionalize the glutamate units are identical to or different from one another and have to the following general formula:

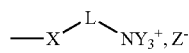

in which:

X=O, NH,

Y=independently H or $CH_3$, $Z^-$=a chloride, a sulfate, a phosphate or an acetate, L=a linear ($C_2$ to $C_6$) alkylene optionally substituted by a functional carboxyl group or derivative thereof.

According to a preferred embodiment, the cationic groups are obtained from compounds selected from the group consisting of: lysine, ornithine, arginine and their derivatives, choline, ethanolamine (linked via the oxygen atom), putrescine and agmatine.

The lysine, ornithine and arginine derivatives can, for example, be ethyl and methyl esters, amides and methylated amides.

Thus, the cationic groups, which can be used in the present invention, can be selected from the following group:

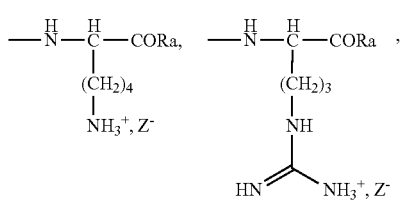

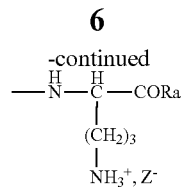

wherein Ra is a hydroxy, alkoxy or alkylamino group, preferably —OMe, —OEt, —$NH_2$, —$NHCH_3$ or —$N(CH_3)_2$, and $Z^-$ is a chloride, a sulfate, a phosphate or an acetate, preferably a chloride, or

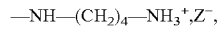

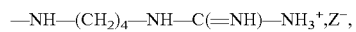

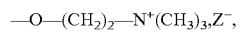

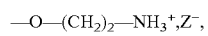

wherein $Z^-$ is a chloride, a sulfate, a phosphate or an acetate, preferably a chloride.

For example, the cationic groups, which can be used in the present invention, can have the following formulae (wherein the name of the precursor is indicated below each group):

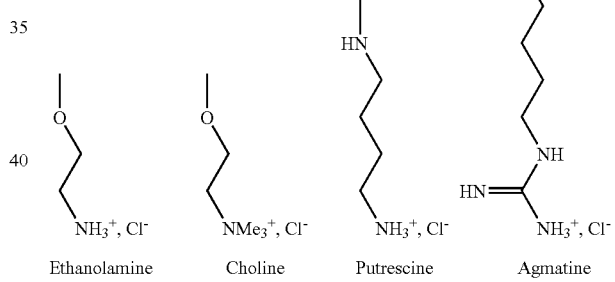

Ethanolamine    Choline    Putrescine    Agmatine

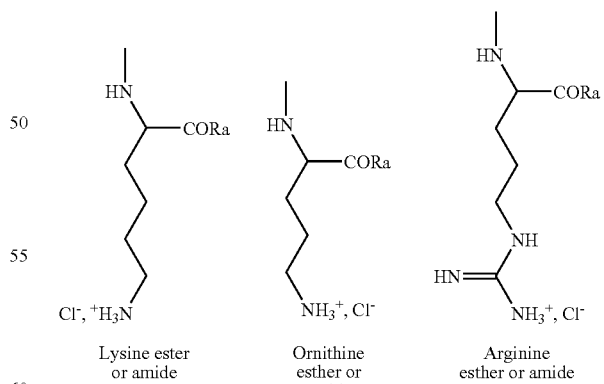

Lysine ester or amide    Ornithine ester or amide    Arginine ester or amide in which Ra represents a hydroxy, alkoxy or alkylamino group, preferably an —OMe, —OEt, —$NH_2$, —$NHCH_3$ or —$N(CH_3)_2$ group.

According to a preferred embodiment, the polyamino acids of the invention comprise, on average, at least 3 hydrophobic groups (GH) per polymer chain.

Advantageously, at least one of the hydrophobic groups GH is included in a hydrophobic graft comprising at least one spacing joint (or unit) (spacer) which makes it possible to link a hydrophobic group GH to a polyglutamate chain (for example, a polyglutamate backbone main chain). This joint can comprise, e.g., at least one direct covalent bond and/or at least one amide bond and/or at least one ester bond. For example, the joint can belong to the group consisting in particular of: "amino acid" residues other than the constituent monomeric unit of the polyglutamate, aminoalcohol derivatives, polyamine (for example diamine) derivatives, polyol (for example diol) derivatives and hydroxy acid derivatives.

The grafting of GHs to a polyglutamate chain can involve the use of GH precursors that can be attached to the polyglutamate chain.

Precursors of GHs can be, in practice and without limitation, selected from the group consisting of alcohols and amines, these compounds being easily functionalized by a person skilled in the art. The grafting of GHs is disclosed in more detail below in the description of the process for obtaining modified polyamino acids according to the invention.

According to a preferred embodiment, a hydrophobic group GH of a hydrophobic graft comprises from 8 to 30 carbon atoms.

These hydrophobic groups GH are advantageously and carefully selected from the group consisting of:
  linear or branched $C_8$ to $C_{30}$ alkyls which can optionally comprise at least one unsaturation and/or at least one heteroatom,
  $C_8$ to $C_{30}$ alkylaryls or arylalkyls which can optionally comprise at least one unsaturation and/or at least one heteroatom,
  and $C_8$ to $C_{30}$ (poly)cyclic compounds which can optionally comprise at least one unsaturation and/or at least one heteroatom.

The joints which form, with the GHs, hydrophobic grafts can be di-, tri- or tetravalent joints (indeed even pentavalent and more). In the case of a divalent joint, the hydrophobic graft comprises a single GH group, whereas a trivalent joint confers a bifid nature to the hydrophobic graft, that is to say that the graft exhibits two GH "arms". Examples of trivalent joints include, but are not limited to, "amino acid" residues, for example "glutamic acid", or polyol residues, for example glycerol. Thus, two advantageous but nonlimiting examples of hydrophobic grafts comprising bifid GHs are dialkylglycerols and dialkyl glutamates.

Hydrophobic groups GH can, for example, be derived from groups chosen from the group consisting of: octanol, dodecanol, tetradecanol, hexadecanol, octadecanol, oleyl alcohol, tocopherol and cholesterol.

According to another alternative embodiment, polyglutamates according to the invention can also carry at least one graft of polyalkylene (preferably polyethylene) glycol type linked to a glutamate residue.

Preferably, the backbone of a polyglutamate according to the present invention comprises α-L-glutamate and/or α-L-glutamic acid units.

More preferably still, polyglutamates according to the invention have to the following formula (I):

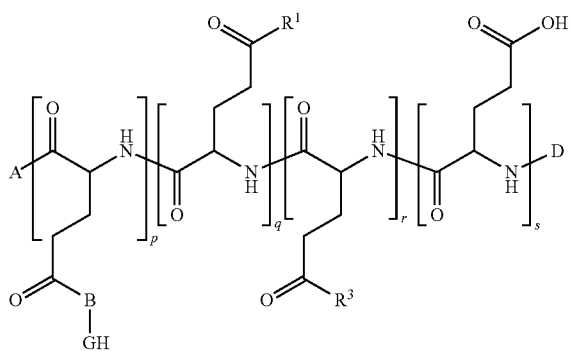

in which:
  A independently represents:
    an RNH— group in which R is H, a linear $C_2$ to $C_{10}$ or branched $C_3$ to $C_{10}$ alkyl or a benzyl group,
    a terminal amino acid residue of formula:

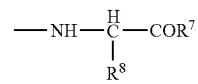

in which
    —$R^7$ is —OH, —$OR^9$ or —$NHR^{10}$, and
    $R^8$, $R^9$ and $R^{10}$ independently are H, a linear $C_2$ to $C_{10}$ or branched $C_3$ and
    $C_{10}$ alkyl group or a benzyl group;
  B is a direct bond or a divalent, trivalent or tetravalent bonding group preferably chosen from the following groups:
    —O—, —NH—, —N($C_1$ to $C_5$ alkyl)-, a residue of amino acid (preferably of a natural amino acid), of diol, of triol, of diamine, of triamine, of aminoalcohol or of hydroxy acid comprising from 1 to 6 carbon atoms;
  D is H, a linear $C_2$ to $C_{10}$ or branched $C_3$ to $C_{10}$ acyl group or a pyroglutamate;
  the hydrophobic groups (GH) each are, independently of one another, a group selected from:
    linear or branched $C_8$ to $C_{30}$ alkyls which can optionally comprise at least one unsaturation and/or at least one heteroatom (preferably O and/or N and/or S), or
    $C_8$ to $C_{30}$ alkylaryls or arylalkyls which can optionally comprise at least one unsaturation and/or at least one heteroatom (preferably O and/or N and/or S), or
    $C_8$ to $C_{30}$ (poly)cyclic compounds which can optionally comprise at least one unsaturation and/or at least one heteroatom (preferably O and/or N and/or S);
    preferably, this group is selected from the group consisting of: octanol, dodecanol, tetradecanol, hexadecanol, octadecanol, oleyl alcohol, tocopherol and cholesterol, B being a direct linked;
  $R^1$ is a radical chosen from the following group of formulae:

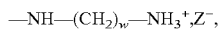

in which w is between 2 and 6, preferably w is 4,

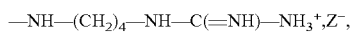

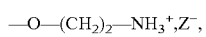

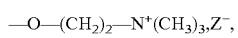

an amino acid residue or an amino acid derivative of formula:

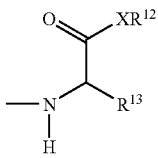

in which:

X is an oxygen atom or —NH—, $R^{12}$ is H, linear $C_2$ to $C_{10}$ or branched $C_3$ to $C_{10}$ alkyl or benzyl, $R^{13}$ is —$(CH_2)_4$—$NH_3^+$, Z, —$(CH_3)_3$—NH—C(=NH)—$NH_3^+$, $Z^-$, —$(CH_2)_3$—$NH_3^+$, $Z^-$;

in which the counteranion $Z^-$ is a chloride, a sulphate, a phosphate or an acetate, preferably a chloride;

$R_3$ is hydroxyethylamino-, alkylene glycol, polyalkylene glycol or a group of formula:

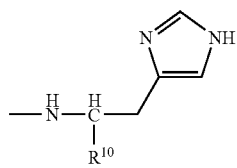

in which —$R^{10}$ is —H, —$CO_2H$, an alkyl ester (preferably —COOMe or —COOEt), —$CH_2OH$, —C(=O)—$NH_2$, —C(=O)—NH—$CH_3$ or —C(=O)—$N(CH_3)_2$;

p, q, r and s are positive integers;

(p)/(p+q+r+s) is defined as the molar degree of grafting of the hydrophobic groups GH and varies from 2 to 99 molar % and preferably between 5 and 50 molar %, provided that each copolymer chain has, on average, at least 3 hydrophobic grafts;

(q)/(p+q+r+s) is defined as the molar degree of grafting of the cationic groups and varies from 1 to 99 molar %;

(p+q+r+s) varies from 10 to 1000, preferably between 30 and 500;

(r)/(p+q+r+s) varies from 0 to 98 molar %;

(s)/(p+q+r+s) varies from 0 to 98 molar % and pharmaceutically acceptable salts thereof.

Preferably, the hydrophobic groups GH and cationic groups are arranged randomly as pendant groups.

Generally, the general formula (I) described above should not be interpreted as representing solely block copolymers but also random copolymers or multiblock copolymers.

Furthermore, it is preferable for the molar degree of grafting of hydrophobic units of the polyglutamates according to the invention to be between 2 and 99% and preferably between 5 and 50%, provided that each polymer chain has, on average, at least 3 hydrophobic grafts.

The ratio (q)/(p+q+r+s) of the polyglutamates according to the invention means that they can comprise from 1 to approximately 97 molar % of groups comprising a cationic charge.

The ratio (s)/(p+q+r+s) of the polyglutamates according to the invention means that they can be anionic, neutral or cationic at neutral pH.

According to another embodiment of the invention, the polymers according to the invention have a molar mass between 2 000 and 200 000 g/mol and preferably between 5000 and 100 000 g/mol.

Obviously, the invention also encompasses mixtures of modified polyamino acids as defined above.

It is worth noting that the polyglutamates of the invention can be used in several ways depending on the nature of the hydrophobic groups and the cationic groups, as well as the charge and the degree of polymerization of the polyglutamate. Methods for forming a polymer for the encapsulation of an active principle in the various forms contemplated by the invention are known to a person skilled in the art. For further details, see, for example, these few particularly relevant references:

"*Microspheres, Microcapsules and Liposomes; Vol. 1. Preparation and Chemical Applications*", edited by R. Arshady, Citus Books, 1999. ISBN: 0-9532187-1-6.

"*Sustained-Release Injectable Products*", edited by J. Senior and M. Radomsky, Interpharm Press, 2000. ISBN: 1-57491-101-5.

"*Colloidal Drug Delivery Systems*" edited by J. Kreuter, Marcel Dekker, Inc., 1994. ISBN: 0-8247-9214-9.

"*Handbook of Pharmaceutical Controlled Release Technology*", edited by D. L. Wise, Marcel Dekker, Inc., 2000. ISBN: 0-8247-0369-3.

Polyglutamates of the invention (in the form of particles or not) can easily associate with or encapsulate active principles, such as proteins, peptides, DNA, RNA or small molecules. The preferred mode of formation is that described in U.S. Pat. No. 6,630,171 delivered to the Applicant, which consists in dispersing the copolymer in water and in incubating the solution in the presence of an active principle (AP). The colloidal solution of vectorization particles composed of the polyglutamates according to the invention can subsequently be filtered through a 0.2 µm filter and then directly injected into a patient.

In cases where the polymer is cationic and soluble in acidic pH due to an excess of cationic charge and that this charge is partially or completely neutralized at neutral pH, such a polymer is said to be dependent on the pH. This type of polymer can thus be used to form a deposit after administration, for example in the subcutaneous tissue.

It should be understood that the residual functional carboxyl groups of a modified polyglutamate are either neutral (COOH form) or ionized ($COO^-$ anion), depending on the pH and the composition. So, both terms i) glutamate residue or residue of glutamic acid, ii) polyglutamic acid or of polyglutamate can be used interchangeably. In aqueous solution, the countercation can be a metal cation, such as sodium, calcium or magnesium, or an organic cation, such as triethanolamine, tris(hydroxymethyl)aminomethane or a polyamine, such as polyethyleneimine. If it is divalent, a countercation can salify two closed monovalent anionic groups.

The counteranion of cationic groups is preferably selected from the group comprising a chloride, a sulfate, a phosphate or an acetate. If it is divalent, a counteranion can salify two closed monovalent cationic groups. Thus, in the present description, the term "pharmaceutically acceptable salts" of the polymer encompasses all polymers with counterions associated with the ionized functions of the polymer. A total or partial neutralization of the charges can also be envisioned for certain structures where positive and negative charges coexist. A polymer having an equivalent number of positive charges and of negative charges (isoelectric point) can exist without the presence either of counteranion or countercation.

The copolymers of the invention may be obtained, for example, using methods known to a person skilled in the art. First of all, it should be remembered that the most widely used technique for obtaining polyamino acids of a type is based on the polymerization of N-carboxyamino acid anhydrides (NCA), described, for example, in the article "*Biopolymers, 1976, 15, 1869*" and in the work by H. R. Kricheldorf, "*alpha-Amino acid N-carboxy Anhydride and related Heterocycles*", Springer Verlag (1987). The NCA derivative is preferably NCA-Glu-O—R₃ (R₃=methyl, ethyl or benzyl). The polymers are subsequently hydrolyzed under conditions appropriate for obtaining the polymer in its acid form. These methods are inspired by the description given in patent FR-A-2 801 226 delivered to the Applicant.

A certain number of polymers which can be used according to the invention, for example poly(α-L-glutamic), poly(α-D-glutamic), poly(α-D,L-glutamate) and poly(γ-L-glutamic) with variable weights, are available commercially.

Preferably, the copolymers of the invention may be synthesized according to two routes. In the first, the cationic group (for example argininamide) and the B-GH group (for example dodecylamine) are first of all grafted, simultaneously or sequentially, to a poly(L-glutamic acid). This reaction can take place in a solvent, such as DMF, DMSO or NMP, according to the following scheme.

In the above mechanism, when q is not zero, the precursor of the R₁ group, such as ethanolamine linked via the nitrogen, is introduced during the synthesis at the same time as the cationic group.

In cases where the cationic group comprises two amine functional groups that are not chemically differentiated (e.g. linear diamine), it can be introduced in a form in which one of the two functional groups is protected. A final stage of cleavage of the protective group is then added to the above scheme.

The poly(L-glutamic acid) can be synthesized according to the route described in patent application FR-A-2 801 226. In cases where the HB-GH group is linked via an ester functional group, it is easier to first graft the B-GH group by a conventional coupling reaction using a carbodiimide, before grafting the cationic group.

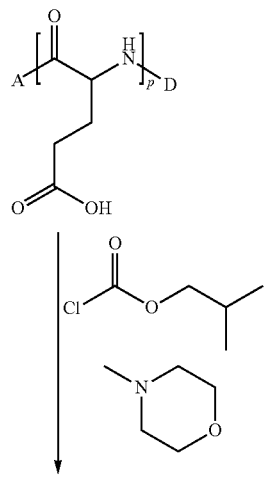

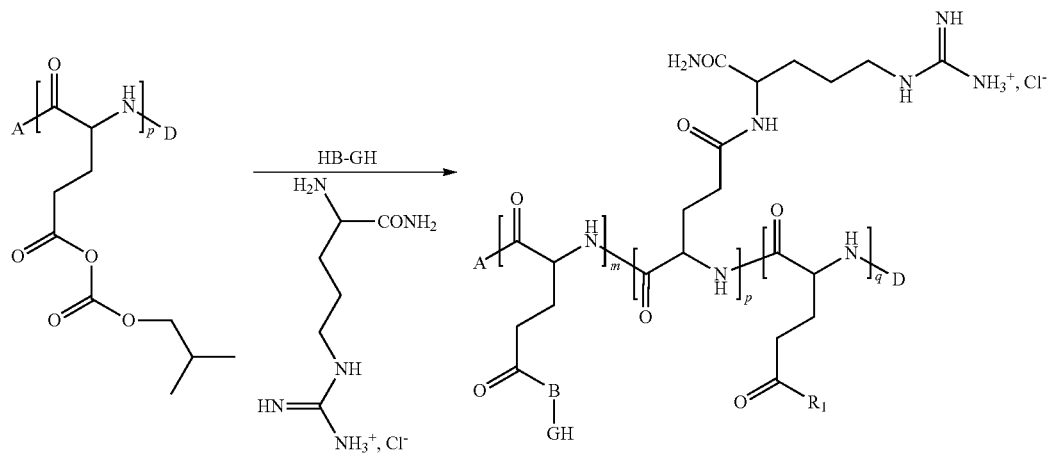

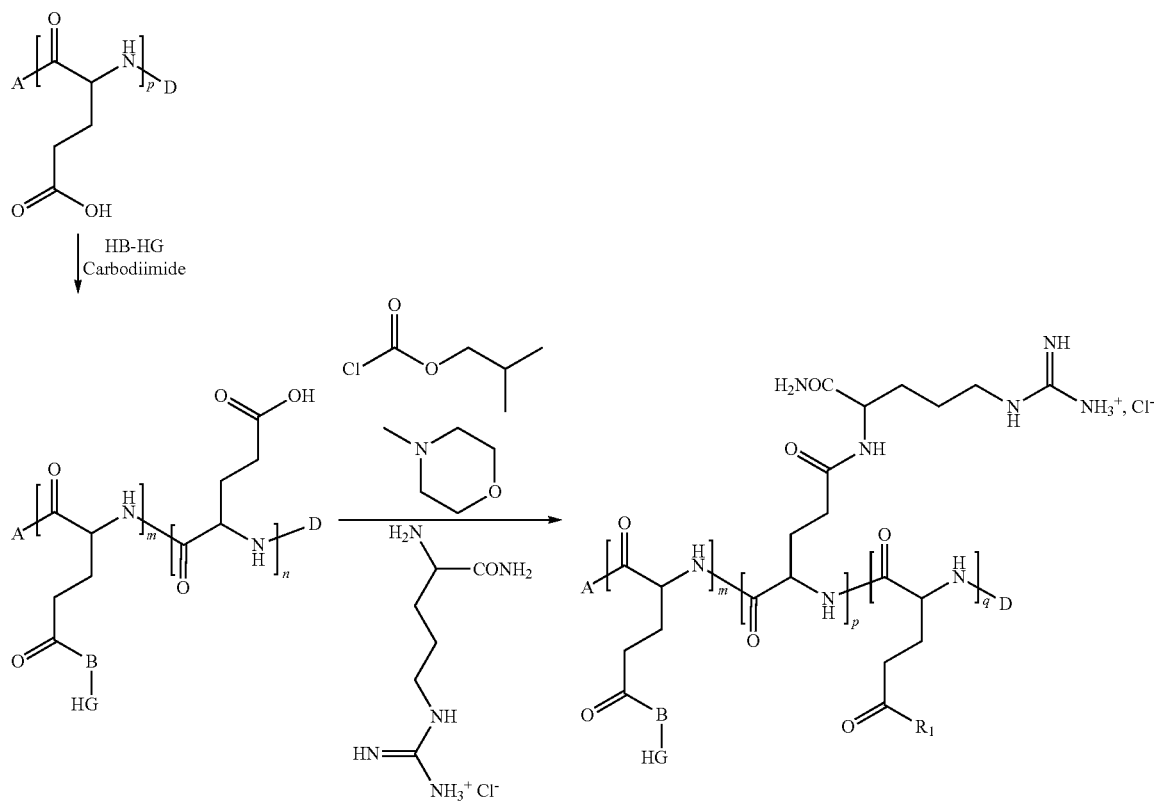

In the above mechanism, when q is not zero, the precursor of the $R_1$ group, such as ethanolamine linked via the nitrogen, is introduced during the synthesis at the same time as the cationic group.

In cases where the cationic group comprises two amine functional groups which are not chemically differentiated (e.g. linear diamine), it can be introduced in a form in which one of the two functional groups is protected. A final stage of cleavage of the protective group is then added to the above scheme.

The polymerization chemistry and the reactions for coupling the groups are conventional methods that are well known to a person skilled in the art (see, for example, the patents or patent applications of the Applicant mentioned above).

These methods will be better understood through the description of the examples.

It should be observed that the degree of polymerization is defined by the molar ratio of the initiator to that of the monomer.

The coupling of a hydrophobic graft GH with an acid group of the polymer is easily carried out by reaction of the polyamino acid in the presence of a carbodiimide as coupling agent and, optionally, a catalyst, such as 4-dimethylaminopyridine, and in an appropriate solvent, such as dimethylformamide (DMF), N-methylpyrrolidone (NMP) or dimethyl sulfoxide (DMSO). The carbodiimide is, for example, dicyclohexylcarbodiimide or diisopropylcarbodiimide. Coupling reagents, such as chloroformates, can also be used for the formation of amide bonds (see, for example, the work by Bodanszky, "Principles of Peptide Synthesis", Springer Verlag, 1984, for examples of coupling agents). The degree of grafting is controlled chemically by the stoichiometry of the constituents and reactants or the reaction time. The hydrophobic grafts functionalized by an amino acid other than that of the polymer are obtained by conventional peptide coupling or by direct condensation by acid catalysis. These techniques are well known to a person skilled in the art.

According to another of its aspects, the invention is directed to a pharmaceutical, cosmetic, health food or plant-protection composition, which comprises at least one polyglutamate as defined above and optionally at least one active principle which can be a therapeutic, cosmetic, health food or plant-protection active principle.

According to an advantageous embodiment of the invention, the active principle is associated with the polyamino acid(s) modified by a cationic group by one or more bonds other than (a) covalent chemical bond(s).

The techniques for associating one or more APs with the modified polyamino acids according to the invention are described in particular in U.S. Pat. No. 6,630,171. They consist in incorporating at least one active principle in the liquid medium comprising Vectorization Particles (VP), so as to obtain a colloidal suspension of VPs charged with or associated with one or more active principle(s) AP(s). This incorporation, which results in trapping of AP by the VPs, can be carried out in the following way:
- aqueous dissolution of AP and then addition of the VPs, either in the form of a colloidal suspension or in the form of isolated VPs (lyophilizate or precipitate);
- or addition of AP, either in solution or in the pure or preformulated state, to a colloidal suspension of VP particles optionally prepared at the time of use by the dispersion of dry VPs in an appropriate solvent, such as water.

Preferably, the active principle is selected from the group consisting of: proteins, glycoproteins, proteins bonded to one or more polyalkylene glycol chains [preferably polyethylene glycol (PEG): "PEGylated proteins"], peptides, polysaccharides, liposaccharides, oligonucleotides, polynucleotides and mixtures thereof, and, more preferably still, from the subgroup of erytropoietins, such as epoetin alfa, epoetin beta, darbepoetin, hemoglobin raffiner, their analogs or their derivatives; oxytocin, vasopressin, adrenocorticotropic hormone, epidermal growth factor, platelet-derived growth factor (PDGF), factors which stimulate hematopoiesis and mixtures thereof, blood factors, such as alteplase, tenecteplase, factor VII(a) or factor VII; hemoglobin, cytochromes, albumins, prolactin, luliberin, luteinizing hormone-releasing hormone (LHRH) and analogs, such as leuprolide, goserelin, triptorelin, buserelin or nafarelin; LHRH antagonists, LHRH competitors, human, porcine or bovine growth hormones (GHs), growth hormone-releasing factor, insulin, somatostatin, glucagon, interleukins or their mixtures (IL-2, IL-11, IL-12), interferons, such as interferon alfa, alfa-2b, beta, beta-1a or gamma; gastrin, tetragastrin, pentagastrin, urogastrone, secretin, calcitonin, enkephalin, endomorphins, angiotensins, thyrotropin-releasing hormone (TRH), tumor necrosis factor (TNF), nerve growth factor (NGF), growth factors, such as beclapermin, trafermin, ancestim or keratinocyte growth factor, granulocyte-colony stimulating factor (G-CSF), granulocyte-macrophage-colony stimulating factor (GM-CSF), macrophage-colony stimulating factor (M-CSF), heparinase, bone morphogenetic protein (BMP), hANP, glucagon-like peptide (GLP-1), VEG-F, recombinant hepatitis B surface antigen (rHBsAg), renin, cytokines, bradykinin, bacitracins, polymyxins, colistins, tyrocidine, gramicidins, etanercept, imiglucerase, drotrecogin alfa, cyclosporins and synthetic analogs, pharmaceutically active modifications and fragments of enzymes, of cytokines, of antibodies, of antigens and of vaccines, and antibodies, such as rituximab, infliximab, trastuzumab, adalimumab, omalizumab, tositumomab, efalizumab and cetuximab.

Other suitable active principles are polysaccharides (for example, heparin) and oligo- or polynucleotids, DNA, RNA, iRNA, antibiotics and living cells.

Another category of suitable active principles comprises pharmaceutical substances which act on the central nervous system, for example risperidone, zuclopenthixol, fluphenazine, perphenazine, flupentixol, haloperidol, fluspirilene, quetiapine, clozapine, amisulprid, sulpiride, ziprasidone, and the like.

According to an alternative form, the active principle is a hydrophobic, hydrophilic or amphiphilic small organic molecule. Within the meaning of the present account, a "small" molecule is in particular a small nonprotein molecule.

Examples of APs that can associate with polyamino acids according to the invention, whether or not in the form of (nano- or micro)particles, include, but are not limited to:
  proteins, such as insulin, interferons, growth hormones, interleukins, erythropoietin or cytokines;
  peptides, such as leuprolide or cyclosporin;
  small molecules, such as those belonging to the family of the anthracyclines, taxoids or camptothecins;
  and mixtures thereof.

Advantageously, the active principle is selected from at least one of the following families of active substances: agents for the treatment of alcohol abuse, agents for the treatment of Alzheimer's disease, anesthetics, agents for the treatment of acromegaly, analgesics, antiasthlmatics, agents for the treatment of allergies, anticancer agents, antiinflammatories, anticoagulants and antithrombotics, anticonvulsants, antiepileptics, antidiabetics, antiemetics, antiglaucomas, antihistaminics, antiinfectives, antibiotics, antifungals, antivirals, antiparkinsonians, anticholinergics, antitussives, carbonic anhydrase inhibitors, cardiovascular agents, hypolipidemics, antiarythnmics, vasodilators, antianginals, antihypertensives, vasoprotectants, cholinesterase inhibitors, agents for the treatment of disorders of the central nervous system, stimulants of the central nervous system, contraceptives, fertility promoters, inducers and inhibitors of uterine labor, agents for the treatment of mucoviscidosis, dopamine receptor agonists, agents for the treatment of endometriosis, agents for the treatment of erectile dysfunctions, agents for the treatment of fertility, agents for the treatment of gastrointestinal disorders, immunomodulators and immunosuppressants, agents for the treatment of memory disorders, antimigraines, muscle relaxants, nucleoside analogs, agents for the treatment of osteoporosis, parasympathomimetics, prostaglandins, psychotherapeutic agents, sedatives, hypnotics and tranquilizers, neuroleptics, anxiolytics, psychostimulants, antidepressants, agents for dermatological treatments, steroids and hormones, amphetamines, anorectics, nonanalgesic painkillers, barbiturates, benzodiazepines, laxatives, psychotropics and any combination of these products.

According to one embodiment, a composition of the invention is in the form of a gel, solution, emulsion, micelles, nanoparticles, microparticles, implant, powder, suspension or film.

According to one of its particularly preferred forms, a composition, loaded or not with active principle(s), is a stable colloidal suspension of polyamino acid nanoparticles and/or microparticles and/or micelles in an aqueous or oily phase.

Microparticles can be obtained by various methods, such as coacervation in the presence of an aggregating agent (divalent or trivalent ions or polyelectrolytes), precipitation by change in pH or in the ionic strength, extraction/evaporation or atomization.

In particular, the composition according to the invention can be a colloidal solution of nanoparticles in an aqueous phase at acidic pH which precipitates at physiological pH.

Advantageously, a polyamino acid of the invention exhibiting an excess of cationic charges can condense an anionic active principle, such as DNA, a DNA fragment, an RNA or an oligo-RNA, in the form of nano- or microparticles and these particles can be internalized in a cell.

According to another embodiment, the composition of the invention is in the form of a solution in a biocompatible solvent and can be injected subcutaneously or intramuscularly or into a tumor.

The composition according to the invention, as it is a pharmaceutical composition, can be administered orally, parenterally, nasally, vaginally, ocularly, subcutaneously, intravenously, intramuscularly, intradermally, intraperitoneally, intracerebrally or buccally or by the pulmonary route.

It can also be contemplated for the composition to be in the form of a solution in a biocompatible solvent or a mixture of biocompatible solvents capable of being injected subcutaneously or intramuscularly or into a tumor.

According to another embodiment, the composition can optionally comprise an excipient for the adjustment of the pH and/or of the osmolarity and/or for improving the stability (antioxidants) and/or as antimicrobial agent. These excipients are well known to a person skilled in the art (reference is made to the work: *Injectable Drug Development*, P. K. Gupta et al., Interpharm Press, Denver, Colo., 1999).

The invention is also directed to a process for the preparation
  of medicaments, in particular for oral, nasal, vaginal, ocular, subcutaneous, intravenous, intramuscular, intradermal, intraperitoneal or intracerebral administration, wherein the active principles of these medicaments can be in particular proteins, glycoproteins, proteins linked to one or more polyalkylene glycol chains {for example, PolyEthylene Glycol (PEG); the term then used is "PEGylated" proteins}, peptides, polysaccharides, liposaccharides, oligonucleotides, polynucleotides and hydrophobic, hydrophilic or amphiphilic small organic molecules;

and/or nutriments;

and/or cosmetic or plant-protection products;

wherein the process consists essentially in employing at least one of the polyamino acids as defined above and/or the composition described above.

The invention also relates to a therapeutic method of treatment which consists essentially in administering the composition as described in the present account orally, parenterally, nasally, vaginally, ocularly, subcutaneously, intravenously, intramuscularly, intradermally, intraperitoneally, intracerebrally or buccally or by the pulmonary route.

According to a specific alternative form of the invention, this therapeutic method of treatment consists essentially in employing the composition as described above in the form of a solution in a biocompatible solvent and then in injecting it subcutaneously or intramuscularly or into a tumor, preferably so that it forms a deposit on the injection site.

The invention will be better understood and its advantages and alternative embodiments will clearly emerge from the examples which follow and which describe the synthesis of the polymers of the invention, their conversion into an AP vectorization system (stable aqueous colloidal suspension) and the demonstration of the ability of such a system to join together with a protein to form pharmaceutical compositions.

EXAMPLES

Example 1

Synthesis of the Polymer (1)

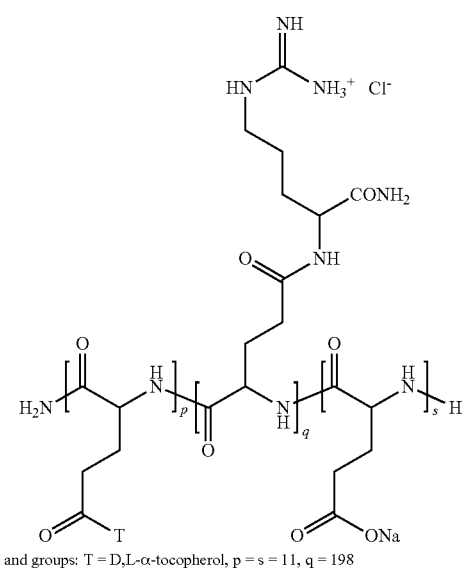

Indices and groups: T = D,L-α-tocopherol, p = s = 11, q = 198

Ten grams of a poly(glutamic acid) with a DP of 220 randomly grafted with 5% of racemic α-tocopherol are dissolved in 125 ml of NMP at 80° C. This solution is cooled to 0° C., and 8.7 ml of isobutyl chloroformate and then 7.35 ml of N-methylmorpholine are added. This reaction mixture is stirred at 0° C. for 15 minutes. At the same time, 24.67 g of argininamide dihydrochloride are suspended in 308 ml of NMP and 14.7 ml of triethylamine are added. The suspension obtained is stirred at 20° C. for a few minutes and then cooled to 0° C. The milky suspension of activated polymer is then added to this suspension and the reaction mixture is stirred at 0° C. for 2 h and then at 20° C. overnight. After addition of 2.1 ml of a 35% HCl solution and then 100 ml of water, the reaction mixture is run dropwise into 1.6 l of water. The solution obtained is diafiltered against 8 volumes of aqueous saline solution (0.9%) and then 4 volumes of water, and concentrated to a volume of approximately 250 ml. The percentage of grafted argininamide, determined by proton NMR in $D_2O$, is 90%.

Example 2

Synthesis of the Polymer (2)

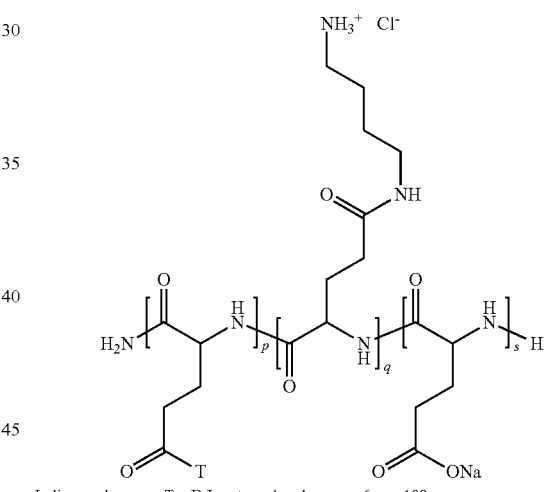

Indices and groups: T = D,L-α-tocopherol, p = s = 6, q = 108

Three and a half grams of a poly(glutamic acid) with a DP of 120 randomly grafted with 5% of racemic α-tocopherol are dissolved in 70 ml of NMP at 80° C. This solution is cooled to 0° C., and 3.2 g of isobutyl chloroformate and then 2.37 g of N-methylmorpholine are added. This reaction mixture is stirred at 0° C. for 10 minutes. At the same time, 4.62 g of N-tert-butyloxycarbonyl-1,4-butanediamine (BOC-putrescine) are dissolved in 9 ml of NMP and then cooled to 0° C. The milky suspension of activated polymer is then added to this solution and the reaction mixture is stirred at 0° C. for 2 h and then at 20° C. overnight. After adding 0.7 ml of a 35% HCl solution, the reaction mixture is run dropwise into 317 ml of water. The solution obtained is adjusted to pH=7.4 with 1N sodium hydroxide solution and then dialyzed against aqueous saline solution (0.9%) and then water. The suspension obtained is lyophilized to give 4.1 g of a white powder. This powder is redissolved in TFA and the solution is stirred at 20° C. for 2 h and then run dropwise into a heel of water while adjusting the pH to approximately 7 with a 1N sodium hydroxide solution. The solution obtained is diafiltered against 8 volumes of aqueous saline solution (0.9%) and then 4 volumes of water, and concentrated to a volume of approximately 50 ml. The percentage of grafted BOC-putrescine, determined by proton NMR in D$_2$O, is 90%.

Example 3

Synthesis of the Polymer (3)

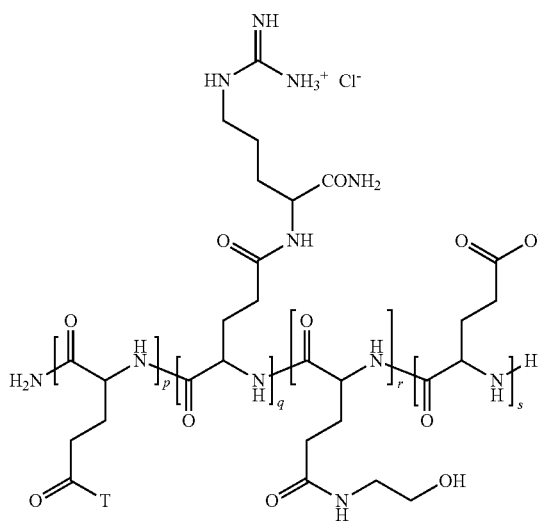

Indices and groups: T = D,L-α-tocopherol, p = 11, q = 88, r = 99, s = 22

Ten grams of a poly(glutamic acid) with a DP of 220 randomly grafted with 5% of racemic α-tocopherol are dissolved in 125 ml of NMP at 80° C. This solution is cooled to 0° C. and 9.1 ml of isobutyl chloroformate and then 7.71 ml of N-methylmorpholine are added. This reaction mixture is stirred at 0° C. for 15 minutes. At the same time, 8.2 g of argininamide dihydrochloride are suspended in 103 ml of NMP and 9.31 ml of triethylamine are added. 1.6 ml of ethanolamine are also added and the suspension obtained is stirred at 20° C. for a few minutes and then cooled to 0° C. The milky suspension of activated polymer is then added to this suspension and the reaction mixture is stirred at 0° C. for 2 h. 1.2 ml of ethanolamine are added and then stirring is carried out at 20° C. overnight. After addition of 2.1 ml of a 35% HCl solution and then 200 ml of water, the reaction mixture is run dropwise into 700 ml of water while adjusting the pH to approximately 7.4. The solution obtained is diafiltered against 8 volumes of aqueous saline solution (0.9%) and then 4 volumes of water, and concentrated to a volume of approximately 250 ml. The percentages of grafted argininamide and of grafted ethanolamine, determined by proton NMR in D$_2$O, are respectively 40 and 45%.

Example 4

Synthesis of the Polymer (4)

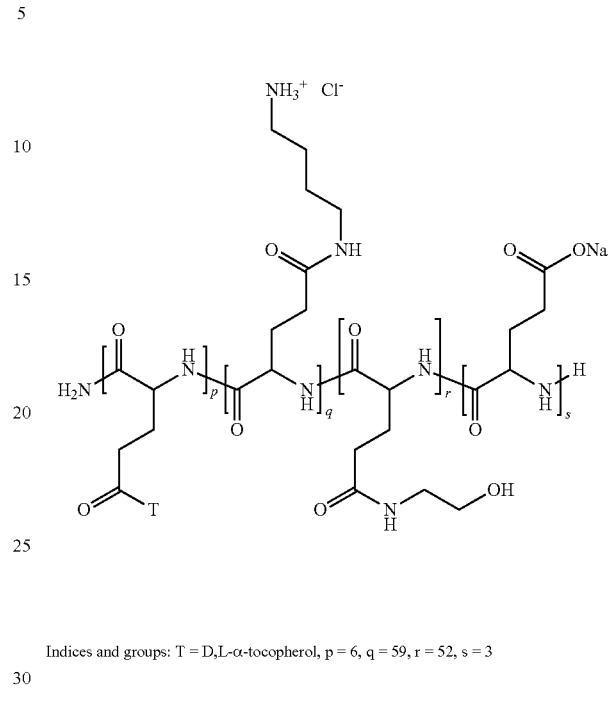

Indices and groups: T = D,L-α-tocopherol, p = 6, q = 59, r = 52, s = 3

Five grams of a poly(glutamic acid) with a DP of 120 randomly grafted with 5% of racemic α-tocopherol are dissolved in 63 ml of NMP at 80° C. This solution is cooled to 0° C. and 4.3 g of isobutyl chloroformate and then 3.7 g of N-methylmorpholine are added. This reaction mixture is stirred at 0° C. for 10 minutes. At the same time, 3.15 g of N-tert-butyloxycarbonyl-1,4-butanediamine (BOC-putrescine) are dissolved in 39 ml of NMP and then cooled to 0° C. This solution is added to the milky suspension of activated polymer and the reaction mixture is stirred at 0° C. for 2 h. 2 ml of ethanolamine are added and then stirring is carried out at ambient temperature overnight. After addition of 1.04 ml of a 35% HCl solution, the reaction mixture is run dropwise into 407 ml of water. The suspension obtained is adjusted to pH=7.4 with 1N sodium hydroxide solution and then dialyzed (cut-off threshold of 1 kD) against aqueous saline solution (0.9%) and then water. The suspension obtained is lyophilized to give a white powder. This powder is redissolved in 100 ml of TFA and the solution is stirred at 20° C. for 1 h 15 and then run dropwise into a heel of water (500 ml) while adjusting the pH to approximately 7 with a 1N sodium hydroxide solution. After addition of 600 ml of ethanol, the solution obtained is diafiltered against 8 volumes of aqueous saline solution (0.9%) and then 4 volumes of water, and concentrated to a volume of approximately 100 ml. The percentages of grafted BOC-putrescine and of grafted ethanolamine, determined by proton NMR in D$_2$O, are respectively 49 and 43%.

Example 5

Synthesis of the Polymer (5)

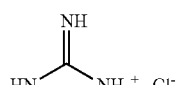
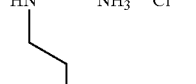
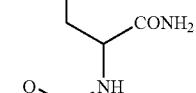
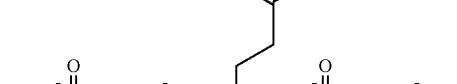
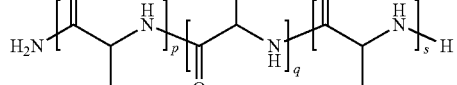

Indices and groups: T = D,L-α-tocopherol, p = 5, q = 83, s = 12

Approximately 300 ml of a 48 mg/g concentrated solution are obtained, according to a procedure similar to that used for the synthesis of the polymer (1), starting from 10 g of a poly(glutamic acid) with a DP of 100 randomly grafted with 5% of racemic α-tocopherol, from 9.6 g of isobutyl chloroformate, from 7.7 ml of N-methylmorpholine, from 24.7 g of argininamide dihydrochloride and from 14.7 ml of triethylamine. The percentage of argininamide, determined by proton NMR in $D_2O$, is 83%.

Example 6

Synthesis of the Polymer (6)

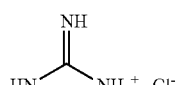
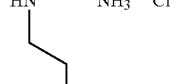
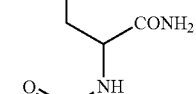
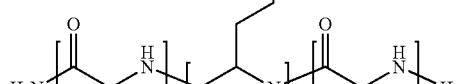
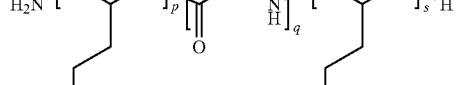

Indices and groups: T = D,L-α-tocopherol, p = 11, q = 62, s = 147

Approximately 250 ml of a 43 mg/g concentrated solution are obtained, according to a procedure similar to that used for the synthesis of the polymer (1), starting from 10 g of a poly(glutamic acid) with a DP of 220 randomly grafted with 5% of racemic α-tocopherol, from 2.9 g of isobutyl chloroformate, from 2.2 ml of N-methylmorpholine, from 4.93 g of argininamide dihydrochloride and from 3.3 ml of triethylamine. The percentage of argininamide, determined by proton NMR in $D_2O$, is 28%.

Example 7

Synthesis of the Polymer (7)

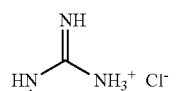
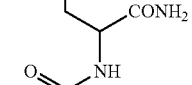
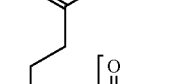
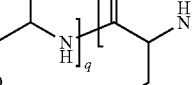
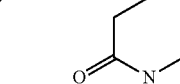
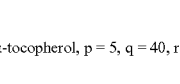
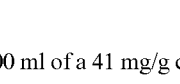
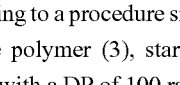
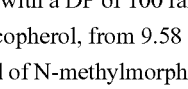

Indices and groups: T = D,L-α-tocopherol, p = 5, q = 40, r = 48, s = 7

Approximately 200 ml of a 41 mg/g concentrated solution are obtained, according to a procedure similar to that used for the synthesis of the polymer (3), starting from 10 g of a poly(glutamic acid) with a DP of 100 randomly grafted with 5% of racemic α-tocopherol, from 9.58 g of isobutyl chloroformate, from 7.7 ml of N-methylmorpholine, from 8.22 g of argininamide dihydrochloride, from 2.86 g of ethanolamine and from 5.1 ml of triethylamine. The percentages of argininamide and of ethanolamine, determined by proton NMR in $D_2O$, are respectively 40 and 48%.

Example 8

Synthesis of the Polymer (8)

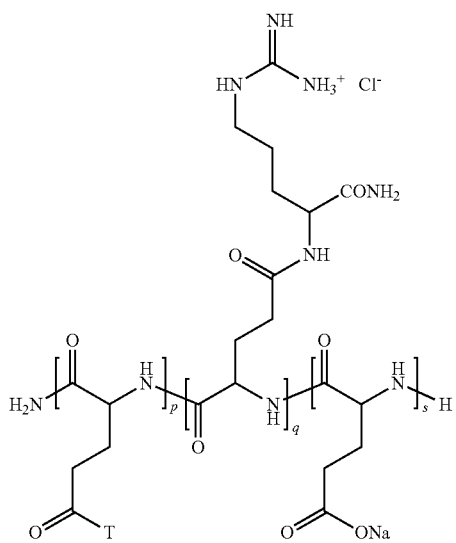

Indices and groups: T = D,L-α-tocopherol, p = 11, q = 139, s = 70

Approximately 200 ml of a 51 mg/g concentrated solution are obtained, according to a procedure similar to that used for the synthesis of the polymer (1), starting from 10 g of a poly(glutamic acid) with a DP of 220 randomly grafted with 5% of racemic α-tocopherol, from 6.39 g of isobutyl chloroformate, from 5.1 ml of N-methylmorpholine, from 13.16 g of argininamide dihydrochloride and from 7.5 ml of triethylamine. The percentage of argininamide, determined by proton NMR in $D_2O$, is 63%.

Example 9

Synthesis of the Polymer (9)

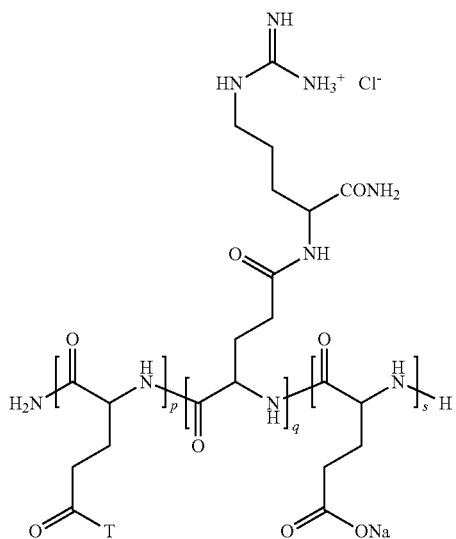

Indices and groups: T = D,L-α-tocopherol, p = 11, q = 121, s = 88

Five grams of a poly(glutamic acid) with a DP of 220 randomly grafted with 5% of racemic α-tocopherol are dissolved in 63 ml of NMP at 80° C. This solution is cooled to 0° C. and 2.38 ml of isobutyl chloroformate and then 2.02 ml of N-methylmorpholine are added. This reaction mixture is stirred at 0° C. for 15 minutes. At the same time, 4.93 g of argininamide dihydrochloride are suspended in 62 ml of NMP and 2.8 ml of triethylamine are added. The suspension obtained is stirred at 20° C. for a few minutes and then cooled to 0° C. The milky suspension of activated polymer is then added to this suspension and the reaction mixture is stirred at 0° C. for 2 h and then at 20° C. for 4 h. After addition of 1.04 ml of a 35% HCl solution and then 50 ml of water, the reaction mixture is run dropwise into 500 ml of an aqueous acidic solution (pH=3) while maintaining the pH at approximately 3-4 with a 1N HCl solution. The solution obtained is diafiltered against 8 volumes of aqueous saline solution (0.9%) and then 4 volumes of water, and concentrated to a volume of approximately 250 ml. The percentage of grafted argininamide, determined by proton NMR in $D_2O$, is 55%.

Example 10

Synthesis of the Polymer (10)

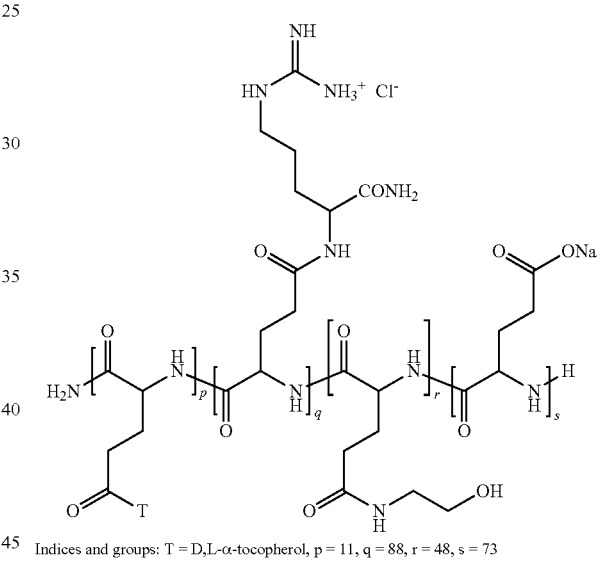

Indices and groups: T = D,L-α-tocopherol, p = 11, q = 88, r = 48, s = 73

Ten grams of a poly(glutamic acid) with a DP of 220 randomly grafted with 5% of racemic α-tocopherol are dissolved in 125 ml of NMP at 80° C. This solution is cooled to 0° C., and 5.6 ml of isobutyl chloroformate and then 4.8 ml of N-methylmorpholine are added. This reaction mixture is stirred at 0° C. for 15 minutes. At the same time, 7.4 g of argininamide dihydrochloride are suspended in 93 ml of NMP and then 4.7 ml of triethylamine and 1.2 ml of ethanolamine are added. The suspension obtained is stirred at 20° C. for a few minutes and then cooled to 0° C. The milky suspension of activated polymer is then added to this suspension and the reaction mixture is stirred at 0° C. for 2 h and then at 20° C. overnight. After addition of 2.07 ml of a 35% HCl solution and then 200 ml of water, the reaction mixture is run dropwise into 670 ml of water acidified to pH=3 with HCl while maintaining the pH at approximately 3 with a 1N HCl solution. The solution obtained is diafiltered against 8 volumes of aqueous saline solution (0.9%) and then 4 volumes of water, and concentrated to a volume of approximately 250 ml. The percentages of grafted argininamide and of grafted ethanolamine, determined by proton NMR in $D_2O$, are respectively 40 and 22%.

Comparative Example 11

The Compound C1 not Functionalized by a Cationic Group

The comparative compound C1 is the precursor (in its anionic form) of the polyglutamate modified by a cationic group, i.e. the polyglutamate with a DP of 220 randomly grafted with 5% of racemic α-tocopherol. This compound is obtained by the method described in application WO-A-03/104303.

Example 12

Study of Association of Insulin

An aqueous solution comprising 10 mg of polymer per milliliter at pH 7.4 and 200 IU of insulin (7.4 mg) is prepared. The solutions are left to incubate at room temperature for two hours and the free insulin is separated from the associated insulin by ultrafiltration (threshold at 100 kDa, 15 minutes under 10 000 G at 18° C.). The free insulin recovered in the filtrate is subsequently assayed by HPLC (High Performance Liquid Chromatography) and the amount of associated insulin is deduced. The results are given in table 1 below.

TABLE 1

| Polymer | % association |
|---------|---------------|
| 3 | 100% |
| 6 | 96% |
| 8 | 100% |
| C1 | 99% |

The results demonstrate that the polymers of the invention can strongly associate with insulin to give colloidal suspensions with a size of greater than 100 kDa and the degrees of association with the insulin are very high. In comparison to polymers C1, it is found that the presence of catalytic charges does not reduce the associated level of insulin.

Example 13

Measurement of the Viscosity (mPa·s) Under Shearing of a 29 mg/g Aqueous Solution with a Rate Gradient of 10 $s^{-1}$

| | Example | | | |
|---|---|---|---|---|
| | C1 | 3 | 6 | 8 | 10 |
| Viscosity | 4720 | 6.6 | 4.5 | 5.8 | 4.7 |

The results demonstrate that the polymers of the invention are markedly less viscous than the reference C1, which does not comprise pendant cationic groups.

Example 14

Study of Solubility as a Function of the pH

The results show that some polymers of the invention (examples 9 and 10) exhibit solubility properties dependent on the pH which, in contrast to the compound C1, allow them to be formulated with an active principle at a moderately acidic pH (pH=4) and to form a deposit at physiological pH (pH in the vicinity of 7).

| Polymer | pH = 4 | Physiological pH |
|---------|--------|------------------|
| 1 | soluble | soluble |
| 2 | soluble | soluble |
| 3 | soluble | soluble |
| 4 | soluble | soluble |
| 5 | soluble | soluble |
| 6 | insoluble | soluble |
| 7 | soluble | soluble |
| 8 | soluble | soluble |
| 9 | soluble | insoluble |
| 10 | soluble | insoluble |
| C1 | insoluble | soluble |

Example 15

Study of Association of a Therapeutic RNA

Associations polymer/RNA in aqueous solution are carried out adding increasing quantities of polymers (1), (3) (two examples of polymers according to the invention which are globally cationic at pH=7.4) or C1 at fixed quantities of a 1433-nucleotides therapeutic RNA. These mixtures are incubated for 2 hours at 37° C., and then analyzed by 1% agarose gel electrophoresis under denaturing conditions (revelation of RNA with ethidium bromide). RNA alone is used as integrity positive control. Incubated RNA with commercial RNAses is used a degraded RNA control.

The results show that when the studied RNA was incubated with polymers (1) or (3), the quantity of RNA, which migrates at the electrophoresis expected size, gradually decreases with the quantity of polymer used for the association and disappears over a certain value without revealing other bands.

In contrast, in the mixture comprising component C1, the quantity of RNA which migrates is unchanged, even with a large excess of polymer.

Secondly, a quantity of polymer (1) or (3) is added to RNA, allowing complete association of the RNA (conditions in which RNA is not visible anymore at the gel expected size) and these mixtures are incubated for 2 hours at 37° C. After 2 hours at 37° C., increasing quantities of compound C1 are added to these mixtures and a new incubation of 16 hours at 37° C. is carried out.

The mixtures obtained are analyzed by 1% agarose gel electrophoresis under denaturing conditions (revelations of RNA with ethidium bromide).

The results show, at the expected size, increasing quantities of RNA in correlation with the quantity of polymer C1 added to the mixture RNA/polymer (1) or (3).

These results show that certain polymers according to the invention, globally cationic at pH=7.4, allow to associate a model RNA with 1433 nucleotides and that this association is reversible with a globally anionic polymer. Moreover, the formulated RNA is not degraded.

Example 16

Study of the Crossing of a Model Oligonucleotide Cellular Membrane

In a Opti-MEM® medium without fetal calf serum, a RNA oligonucleotide of 30 bases marked with Cy3 is mixed with a quantity of polymer (3) or (7) closed to the minimum quantity necessary to totally associate the oligonucleotide. This mixture is contacted on human hepatocarcinom cells Huh-7 grown on 24-well plates with 25 000 cell/well. After 4 hours of cell incubation at 37° C., 5% $CO_2$, medium D-MEM at 20% of fetal calf serum (FCS) is added so as to the final concentration of FCS be 10%. After a 24 hours incubation with oligonucleotide/polymer mixtures, cells are washed, their membranes are marked with biotinyled concanavalin and then cells are fixed for 3 minutes with paraformaldehyde at 3.7%.

After 2 washings with PBS buffer, cells are incubated with DAPI (nuclear DNA) for 10 minutes, washed 3 times with PBS, and then incubated with AlexaFluor®488—marked streptavidine which reveals the biotinyled concanavaline.

Cells are analyzed by confocal microscopy.

Localization of cells is possible by observing AlexaFluor®488—stained streptavidine which reveals the biotinyled concanavaline.

Cells are analyzed by confocal microscopy.

Localization of cells is possible by observing their AlexaFluor®488—stained membrane and their DAPI-stained nucleous.

The uptake of Cy3-labeled oligonucleotide by the cell is visualized by Cy3 fluorescence (excitation at 550 nm, emission at 570 nm).

The results show that Cy3-labeled oligonucleotide is found in the cytoplasm of Huh-7 cells, when the cells were incubated in the presence of the oligonucleotide and polymer (3) or (7). By comparison, when the oligonucleotide was incubated alone, or with polymer C1, no Cy3-labeled oligonucleotide is observed in the cells.

What is claimed is:

1. Polyamino acid, or a pharmaceutically acceptable salt thereof, comprising glutamic residues,
   wherein at least one glutamic residue carries a pendant cationic group which, if it can be deprotonated, exhibits a pKa equal to or greater than 7,
   said pendant cationic groups being identical to or different from one another, and
   wherein at least one glutamic residue carries a pendant nonionizable hydrophobic group (GH), the pendant hydrophobic groups (GH) being identical to or different from one another,
   said hydrophobic groups (GH) being selected from the group consisting of:
   linear or branched $C_8$ to $C_{30}$ alkyls;
   linear or branched $C_8$ to $C_{30}$ alkyl comprising at least one unsaturation or at least one heteroatom;
   $C_8$ to $C_{30}$ alkylaryls or arylalkyls;
   $C_8$ to $C_{30}$ alkylaryls or arylalkyls comprising at least one unsaturation or at least one heteroatom;
   $C_8$ to $C_{30}$ (poly)cyclic compounds; or
   $C_8$ to $C_{30}$ (poly)cyclic compounds comprising at least one unsaturation or at least one heteroatom;
   said pendant cationic groups:
   having the formula of:

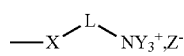

in which:
   X is an O or NH,
   Y is independently an H or $CH_3$,
   $Z^-$ is selected from the group consisting of: a chloride, a sulfate, a phosphate and an acetate,
   L comprises a linear ($C_2$ to $C_6$) alkylene, a linear ($C_2$ to $C_6$) alkylene substituted by a functional carboxyl group,
   or being selected from the group consisting of:

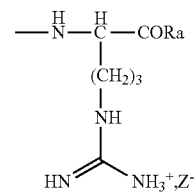

where Ra is a hydroxyl, alkoxy or alkylamino group and $Z^-$ is selected from the group consisting of: a chloride, a sulfate, a phosphate and an acetate,
   —NH—$(CH_2)_4$—NH—C(=NH)—$NH_3^+$, $Z^-$, where $Z^-$ is selected from the group consisting of: a chloride, a sulfate, a phosphate and an acetate.

2. The polyamino acid of claim 1, wherein the pendant cationic groups are grafted to the glutamic residues via an amide or ester bond.

3. The polyamino acid of claim 1 or claim 2, wherein the polyamino acid is composed of L-glutamate or L-glutamic homopolymers linked to the polyamino acid by their carboxy group in alpha position.

4. The polyamino acid of claim 1, wherein the pendant cationic groups are selected from the group consisting of:

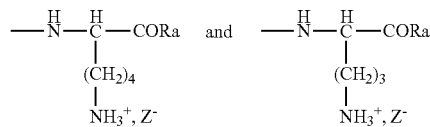

wherein Ra is selected from the group consisting of a hydroxy, alkoxy and alkylamino group, and
   $Z^-$ is selected from the group consisting of a chloride, a sulfate, a phosphate, and an acetate, or

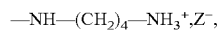

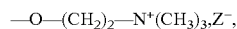

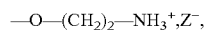

wherein $Z^-$ is a chloride, a sulfate, a phosphate or an acetate.

5. The polyamino acid of claim 1, wherein said polyamino acid comprises at least 3 hydrophobic groups (GH) per polymer chain.

6. The polyamino acid of claim 1, wherein at least one glutamic residue carries a pendant nonionizable group different from the hydrophobic groups (GH), said nonionizable groups being identical to or different from one another.

7. The polyamino acid of claim 6, wherein said pendant nonionizable group is hydroxyethylamino.

8. The polyamino acid of claim 1, wherein at least one glutamic residue carries a group which is nonionized at neutral pH different from the hydrophobic groups (GH).

9. The polyamino acid of claim 8, wherein said group which is nonionized at neutral pH has the following formula:

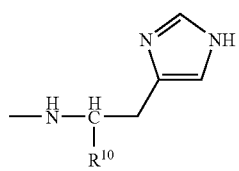

in which —R$^{10}$ is selected from the group consisting of: —H, —CO$_2$H, alkyl ester, —CH$_2$OH, —C(=O)—NH$_2$, —C(=O)—NH—CH$_3$ and —C(=O)—N(CH$_3$)$_2$.

10. The polyamino acid of claim 1, wherein said polyamino acid carries at least one graft of polyalkylene glycol type linked to a glutamate residue.

11. The polyamino acid of claim 1, wherein said polyamino acid has the following formula (I):

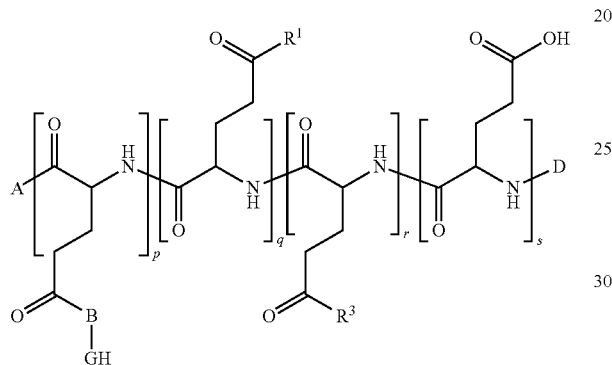

in which:

A independently is:
  RNH— wherein R is selected from the group consisting of: H, a linear C$_2$ to C$_{10}$ alkyl or a benzyl group and branched C$_3$ to C$_{10}$ alkyl or a benzyl group;
  a terminal amino acid residue of formula:

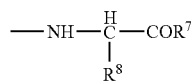

in which —R$^7$ is selected from the group consisting of —OH, —OR$^9$ and —NHR$^{10}$, and R$^8$, R$^9$ and R$^{10}$ independently are selected from the group consisting of: H, a linear C$_2$ to C$_{10}$ or branched C$_3$ and C$_{10}$ alkyl group or a benzyl group;

B is a direct bond or a divalent, trivalent or tetravalent bonding group selected from the group consisting of: —O—, —NH—, —N(C$_1$ to C$_5$ alkyl)-, a residue of amino acid, diol hydroxy acid comprising from 1 to 6 carbon atoms, triol hydroxy acid comprising from 1 to 6 carbon atoms, diamine hydroxy acid comprising from 1 to 6 carbon atoms, triamine hydroxy acid comprising from 1 to 6 carbon atoms, aminoalcohol hydroxy acid comprising from 1 to 6 carbon atoms and hydroxy acid comprising from 1 to 6 carbon atoms;

D is selected from the group consisting of: H, a linear C$_2$ to C$_{10}$ acyl group or a pyroglutamate, branched C$_3$ to C$_{10}$ acyl group and a pyroglutamate;

GH is a hydrophobic group as claimed in claim 1;

R$^1$ is a group selected from the following formulas:

—NH—(CH$_2$)$_w$—NH$_3^+$,Z$^-$, in which w is between 2 and 6,

—NH—(CH$_2$)$_4$—NH—C(=NH)—NH$_3^+$,Z$^-$,

—O—(CH$_2$)$_2$—NH$_3^+$,Z$^-$,

—O—(CH$_2$)$_2$—N$^+$(CH$_3$)$_3$,Z$^-$, an amino acid residue or an amino acid derivative of formula:

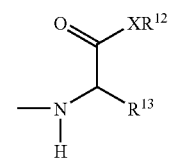

in which:

X is an oxygen atom or —NH—,

R$^{12}$ is selected from the group consisting of: H, linear C$_2$ to C$_{10}$ alkyl or benzyl and branched C$_3$ to C$_{10}$ alkyl or benzyl, R$^{13}$ is selected from the group consisting of: —(CH$_2$)$_4$—NH$_3^+$, Z$^-$; —(CH$_3$)$_3$—NH—C(=NH)—NH$_3^+$, Z$^-$, and —(CH$_2$)$_3$—NH$_3^+$, Z$^-$;

in which the counteranion Z$^-$ is selected from the group consisting of: a chloride, a sulphate, a phosphate and an acetate, R$^3$ is selected from the group consisting of: a hydroxyethylamino, an alkylene glycol, a polyalkylene glycol and a radical of formula:

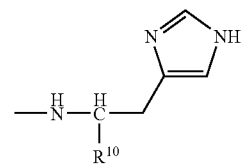

in which —R$^{10}$ is selected from the group consisting of: —H, —CO$_2$H, an alkyl ester, —CH$_2$OH, —C(=O)—NH$_2$, —C(=O)—NH—CH$_3$ and —C(=O)—N(CH$_3$)$_2$;

p, q, r and s are non-negative integers;

(p)/(p+q+r+s) is defined as the molar degree of grafting of the hydrophobic groups GH and varies from 2 to 99 molar % when each copolymer chain has at least 3 hydrophobic grafts;

(q)/(p+q+r+s) is defined as the molar degree of grafting of the cationic groups and varies from 1 to 99 molar %;

(p+q+r+s) varies from 10 to 1000;

(r)/(p+q+r+s) varies from 0 to 98 molar %; and (s)/(p+q+r+s) varies from 0 to 98 molar %.

12. A pharmaceutical, cosmetic, health food or plant-protection composition comprising at least one polyamino acid of claim 1.

13. The composition of claim 12, further comprises at least one active principle.

14. The composition of claim 13, wherein the active principle is associated with the polyamino acid by one or more bonds other than (a) covalent chemical bond(s).

15. The composition of claim 13, wherein the active principle is selected from the group consisting of DNA, a DNA fragment, an RNA and an oligo-RNA.

16. The composition of claim 12, wherein said composition comprises a colloidal suspension of nanoparticles and/or microparticles and/or micelles of polyamino acid in an aqueous or oily phase.

17. The composition of claim 16, wherein the suspension is a colloidal solution of nanoparticles in an aqueous phase at acidic pH which precipitates at physiological pH.

18. A process for the preparation of a medicament, in particular for oral, nasal, pulmonary, vaginal, ocular, subcutaneous, intravenous, intramuscular, intradermal, intraperitoneal or intracerebral administration, said process consisting essentially in employing at least one polyamino acid of claim 1, wherein the active principle of the medicament is selected from the group consisting of: proteins, glycoproteins, proteins bonded to one or more polyalkylene glycol chains, peptides, polysaccharides, liposaccharides, oligonucleotides, polynucleotides and hydrophobic, hydrophilic and amphiphilic small organic molecules, nutriments, cosmetic and plant-protection products.

\* \* \* \* \*